(12) United States Patent
Ji

(10) Patent No.: US 10,201,403 B2
(45) Date of Patent: Feb. 12, 2019

(54) BRACKET, ORTHODONTIC SYSTEM WITH THE BRACKET AND AN ORTHODONTIC METHOD

(71) Applicant: Li Ji, Guangdong (CN)

(72) Inventor: Li Ji, Guangdong (CN)

( * ) Notice: Subject to any disclaimer, the term of this patent is extended or adjusted under 35 U.S.C. 154(b) by 125 days.

(21) Appl. No.: 14/744,840

(22) Filed: Jun. 19, 2015

(65) Prior Publication Data

US 2015/0366639 A1   Dec. 24, 2015

(30) Foreign Application Priority Data

Jun. 20, 2014   (CN) .......................... 2014 1 0281231
Jan. 29, 2015   (CN) .......................... 2015 1 0046947

(51) Int. Cl.
*A61C 7/28*   (2006.01)
*A61C 7/14*   (2006.01)
*A61C 7/34*   (2006.01)

(52) U.S. Cl.
CPC ............... *A61C 7/287* (2013.01); *A61C 7/14* (2013.01); *A61C 7/28* (2013.01); *A61C 7/34* (2013.01)

(58) Field of Classification Search
CPC .. A61C 7/14; A61C 7/28; A61C 7/287; A61C 7/34
See application file for complete search history.

(56) References Cited

U.S. PATENT DOCUMENTS

| | | | |
|---|---|---|---|
| 2007/0128571 A1 | 6/2007 | Kimura | |
| 2009/0325120 A1* | 12/2009 | Lewis | A61C 7/287 433/13 |
| 2011/0020762 A1* | 1/2011 | Kanomi | A61C 7/14 433/10 |
| 2013/0108977 A1 | 5/2013 | Shon et al. | |
| 2014/0178831 A1 | 6/2014 | Foerster | |

FOREIGN PATENT DOCUMENTS

| | | |
|---|---|---|
| CN | 201244093 | 5/2009 |
| CN | 201418798 | 3/2010 |
| CN | 104138299 | 11/2014 |
| CN | 203943752 | 11/2014 |
| WO | 2015192502 | 12/2015 |

OTHER PUBLICATIONS

International Search Report for PCT Appl. No. PCT/CN2014/086717, dated Sep. 17, 2014.

* cited by examiner

*Primary Examiner* — Tammie K Marlen
(74) *Attorney, Agent, or Firm* — Seyfarth Shaw LLP

(57) ABSTRACT

A bracket including a main body part and a covering part. The main body part includes a first surface portion and a first bottom face portion. The first surface portion is provided with a first groove, which divides the first surface portion into first and second ends. The first end has a surface with a first protruding portion having a smooth curved surface. The covering part includes a second surface portion and a second bottom face portion, the second bottom face portion matches with the surface of the second end, and the second surface portion has a smooth curved surface matching the surface of the first protruding portion. The covering part and the main body part are adapted to match and be engaged with each other to form the bracket having a smooth curved shape in a gingival direction, an occlusal direction, a mesial direction and a distal direction.

16 Claims, 14 Drawing Sheets

BRACKET, ORTHODONTIC SYSTEM WITH THE BRACKET AND AN ORTHODONTIC METHOD

CROSS-REFERENCE TO RELATED APPLICATIONS

The present application claims priority to Chinese Patent Application No. CN201410281231.4, filed Jun. 20, 2014, and Chinese Patent Application No. CN201510046947.0, filed Jan. 29, 2015, the disclosures for which are hereby incorporated herein in their entireties by reference.

FIELD

The present disclosure relates generally to a fix-appliance of orthodontic technique and the field of orthodontics, and more particularly, to a bracket, orthodontics system with the bracket and an orthodontic method.

BACKGROUND

As an important unit in the fix-appliance technique, a bracket is a correction instrument for correcting deformity of the teeth. The bracket can be bonded directly to the surface of dental crowns, and various types of orthodontic forces can be applied to the tooth by an arch wire via the bracket, so as to realize orthodontic treatment.

At present, all of the traditional brackets are square, with a protruding limb for fixing the arch wire provided on each corner of the bracket. The mucous membrane of a patient's mouth may be stung by the protruding limb and the patient may feel uncomfortable. In addition, food, such as vegetable leaves, may be retained by the bracket when the patient is eating, which can be detrimental for oral health, or may even cause more accumulation of tartar and dental plaque.

SUMMARY

In view of the problems existing in the prior art, it is an object of the present disclosure to provide a bracket that is comfortable for use in a patient's mouth, is beneficial for oral hygiene and reduces tooth demineralization and caries around the bracket.

According to an aspect of the present disclosure, a bracket is provided, including:

a main body part, including a first surface portion and a first bottom face portion, wherein the first surface portion has a first groove dividing the first surface portion into first and second ends, and the first end has a surface with a first protruding portion; and a covering part, including a second surface portion and a second bottom face portion, wherein the second bottom face portion matches with the surface of the second end of the main body part; and wherein the first protruding portion has an outside surface in a shape of a smooth curved surface, and the second surface portion of the covering part is smooth, curved and matches with the outside surface of the first protruding portion; the covering part and the main body part are adapted to be engaged with each other to form the bracket that is in a smooth curved shape in a gingival direction, an occlusal direction, a mesial direction and a distal direction. In the bracket according to the present disclosure, the main body part and the covering part are adapted to match and be engaged with each other, and the smooth curved surface of the first protruding portion and the smooth curved second surface portion of the covering part are adapted to match with each other. Thus, a surface of the bracket facing the mouth and the lips is smooth, and will not sting the mucous membrane of the patient's mouth like a bracket with a limb, making the patient feel comfortable. Because the bracket according to the present disclosure does not have a protruding limb, food, such as vegetable leaves, may not be retained in the bracket when the patient is eating, which is beneficial for oral health. The smooth curved surface can reduce the accumulation of tartar and dental plaque, and is beneficial for oral cleaning because it is easy to clean the bottom of the bracket. In addition, the bracket according to the present disclosure can reduce the demineralization of the tooth around the bracket and caries.

In one embodiment, the first protruding portion has a smooth curved surface, the second surface portion of the covering part is smooth and curved, the covering part and the main body part are adapted to match and be engaged with each other to form the bracket that is in a shape of ellipsoid or sphere in a gingival direction, an occlusal direction, a mesial direction and a distal direction.

In one embodiment, when the covering part is engaged with the main body part, an inner surface of the covering part matches with an opposing inner surface of the main body part, and an outer surface of the covering part and an outer surface of the main body part form the smooth curved shape.

In one embodiment, a side surface of the first protruding portion facing the first groove is provided with a second groove, and a side surface of the covering part facing the main body part is provided with a protruding rim that matches with the second groove. In this way, the covering part and the main body part can be interlocked with each other to prevent slipping.

In one embodiment, the first end of the main body part is provided with a through hole, and one end of the through hole opens at the second groove. When the covering part cannot be removed from the main body part, a sharp tool may be inserted into the through hole and pass through the through hole to reach the protruding rim of the covering part, and the covering part may be removed from the main body part by pushing the covering part away from the main body part with the sharp tool.

In one embodiment, the second end of the main body part is provided on its surface with a first bulge having a top size larger than its bottom size; and the second bottom face portion of the covering part is provided with a third groove of an elongated shape, the third groove has a opening size smaller than its inner size, and the opening of the third groove is provided with a window that matches with the first bulge and is adapted receive the first bulge. Having a top size larger than its bottom size, the first bulge has a concave structure that is adapted to fix the third groove of the covering part to prevent the dislocation of the covering part.

In one embodiment, the first bulge is in a shape of a cylinder, the top end of the first bulge is provided with a ball structure with a diameter larger than that of the first bulge. Compared with other structures, the ball structure with a spherical shape can slide more smoothly in the third groove, to facilitate the covering part being installed into or removed from the main body part.

In one embodiment, all of edges of the first end of the main body part are protruded to form the first protruding portion. This can avoid scratching of the mouth and lips caused by the edges and corners of the main body part, so that the food, such as vegetable leaves, may not be retained, which is beneficial for oral hygiene.

In one embodiment, the bracket further includes a base plate including a third surface portion and a third bottom face portion, the main body part is adapted to be fixed on the third surface portion of the base plate, the edge of one side of the main body part facing the third surface portion of the base plate is provided with a first recess, and the first recess and the base plate form a fourth groove; and there are at least two fourth grooves evenly distributed on the edge of one side of the main body part facing the third surface portion of the base plate, which is convenient for ligature wire being ligatured in the fourth grooves.

In one embodiment, outer edges of the fourth grooves are respectively provided with a second bulge facing the base plate. An outer edge of the fourth groove and the second bulge form a protruding limb to mainly prevent the ligature wire ligatured in the fourth groove from dislocating and moving.

In one embodiment, the second surface portion of the covering part facing an edge of the main body part is provided with a second recess adapted to receive a finger to control the assembly and disassembly of the covering part and the main body part.

In one embodiment, the bracket further includes a connection part, the main body part and the covering part are connected by the connection part; a side surface of the first end of the main body part facing the second end of the main body part is provided with a fifth groove having an opening size smaller than its inner size, and a side surface of the covering part facing the fifth groove of the main body part is provided with a sixth groove having an opening size smaller than its inner size; and the connection part includes a first connection side matching with the fifth groove, and a second connection side matching with the sixth groove.

In one embodiment, the fifth groove is semicircular in cross section along the first groove.

In one embodiment, the sixth groove is rectangular in cross section along the first groove, and one edge of the opening of the sixth groove has a protruding border extending towards the other edge; and the first connection side of the connection part has a shape of a semi-cylinder that matches with the semicircular cross section of the fifth groove, the second connection side of the connection part has an L-shape that matches with the sixth groove, and the first connection side is located at an end of the second connection side.

In one embodiment, the surface of the second end of the main body part is connected with a second protruding portion having a top size larger than its bottom size; and a side surface of the covering part facing the first end is provided with a groove portion, and the groove portion has a first opening on a side surface of the groove portion facing the first end, and a second opening on the second bottom face portion of the covering part, the size of the first opening matches with that of the second protruding portion.

In one embodiment, both sides of the top of the second protruding portion protrude outwards to make the second protruding portion in a T-shape, and the first opening is in a T-shape.

In one embodiment, the bracket further includes a base plate connected to the first bottom face portion of the main body part, the edge of one side of the main body part facing the base plate is provided with a recess, and the recess and the base plate form a ligaturing groove; and there are at least two ligaturing grooves, the ligaturing grooves are evenly distributed on the edge of one side of the main body part facing the base plate, and outer edges of the recess are respectively provided with a bulge facing the base plate to form a protection limb.

In one embodiment, the first end of the main body part is provided with a safety hole, one end of the safety hole opens at the surface of the first end of the main body part, and the other end of the safety hole opens at a side surface of the first end of the main body part facing the covering part.

It is an additional object of the present disclosure to provide an orthodontics system with a bracket.

According to another aspect of the present disclosure, an orthodontics system includes an arch wire and a bracket as mentioned above.

It is a further object of the present disclosure to provide an orthodontic method.

According to a further aspect of the present disclosure, an orthodontic method includes:

adhering and fixing a main body part of a bracket of an orthodontics system onto a surface of the tooth of a patient;

threading an arch wire of the orthodontics system through a first groove of the main body part of the bracket of the orthodontics system; and fixing a covering part of the bracket of the orthodontics system on a second end of the main body part in a matching manner, the first groove of the main body part and the arch wire being covered by the covering part, and a surface of a first protruding portion of the first end of the main body part and a surface portion of the covering part are combined to form a smooth curved shape.

The bracket according to the present disclosure is easy to use in operation; the device is easy to be produced and operated with low cost, and is safe in use, saving time and manpower.

DETAILED DESCRIPTION OF THE PREFERRED EMBODIMENTS

In the following description of embodiments, reference is made to the accompanying drawings which form a part hereof, and in which it is shown by way of illustration specific embodiments of the disclosure that can be practiced. It is to be understood that other embodiments can be used and structural changes can be made without departing from the scope of the disclosed embodiments.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Example One

As shown in FIGS. 1-13, a bracket includes a main body part 10 and a covering part 20.

Figure 1:
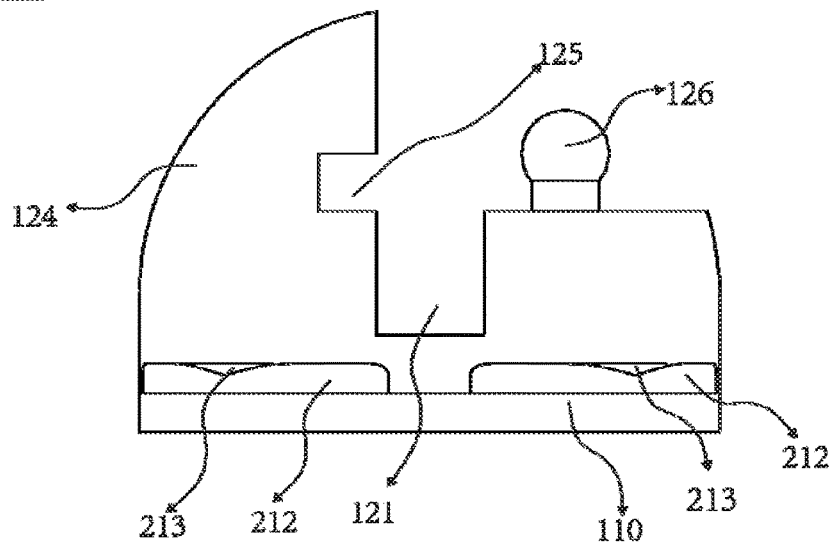
FIG. 1 is a side view illustrating a main body part according to Example One of the present disclosure.
Figure 2:
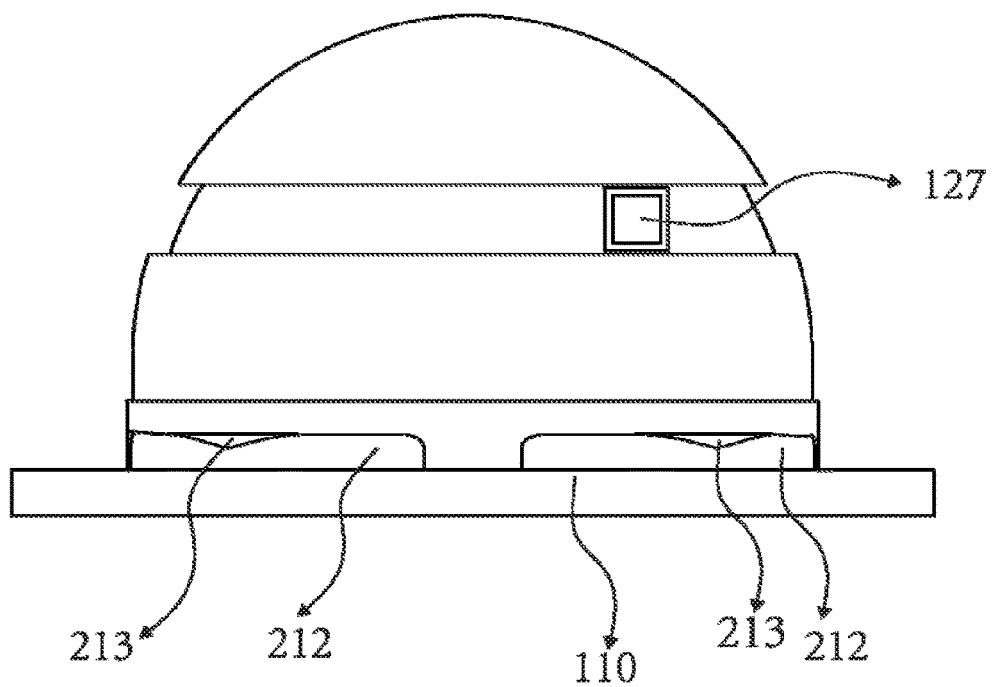
FIG. 2 is a side view illustrating a main body part according to Example One of the present disclosure.
Figure 3:
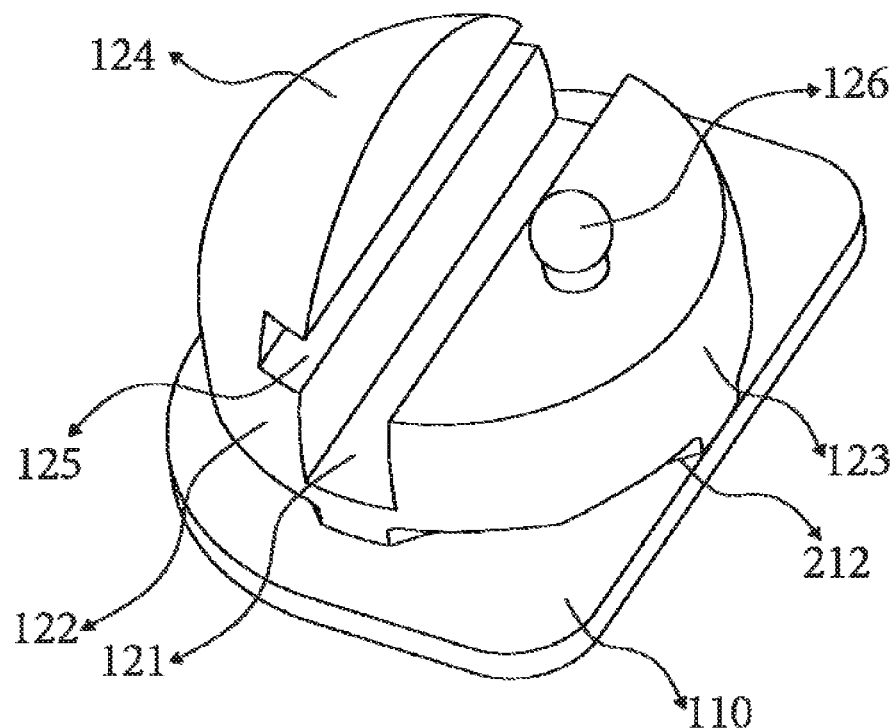
FIG. 3 is a plan view illustrating a main body part according to Example One of the present disclosure.
Figure 4:
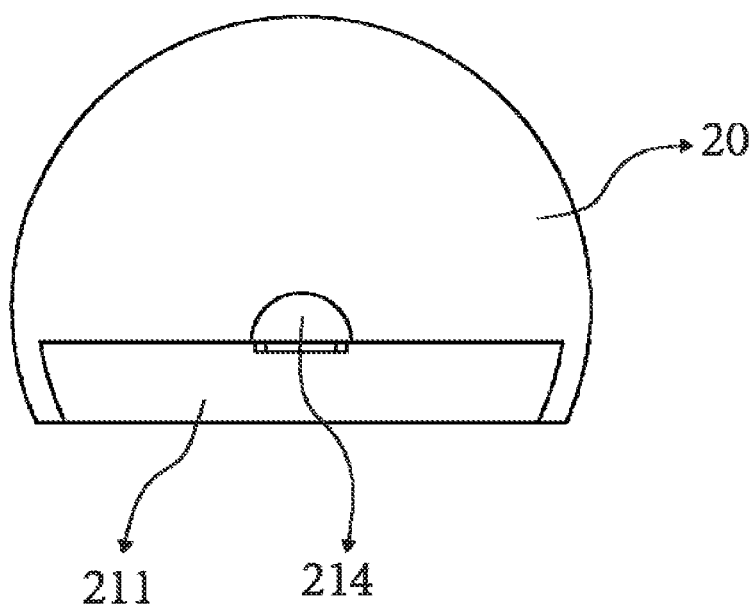
FIG. 4 is a top view illustrating a main body part according to Example One of the present disclosure.
Figure 5:
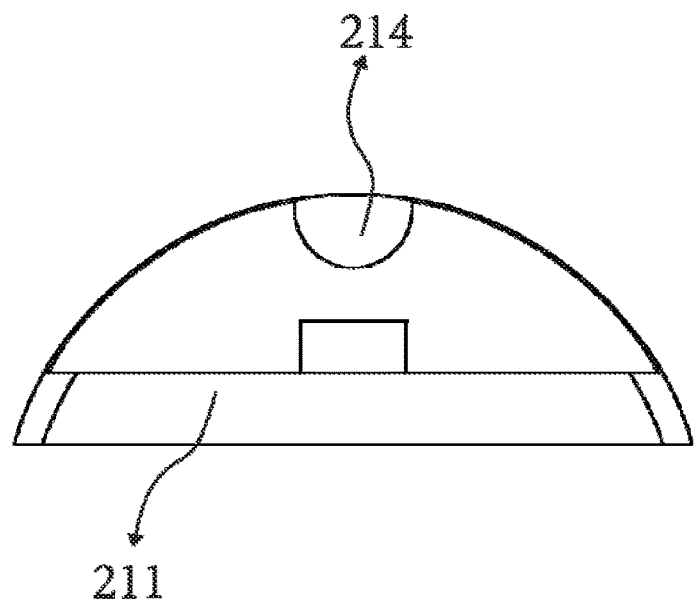
FIG. 5 is a side view illustrating a covering part according to Example One of the present disclosure.
Figure 6:
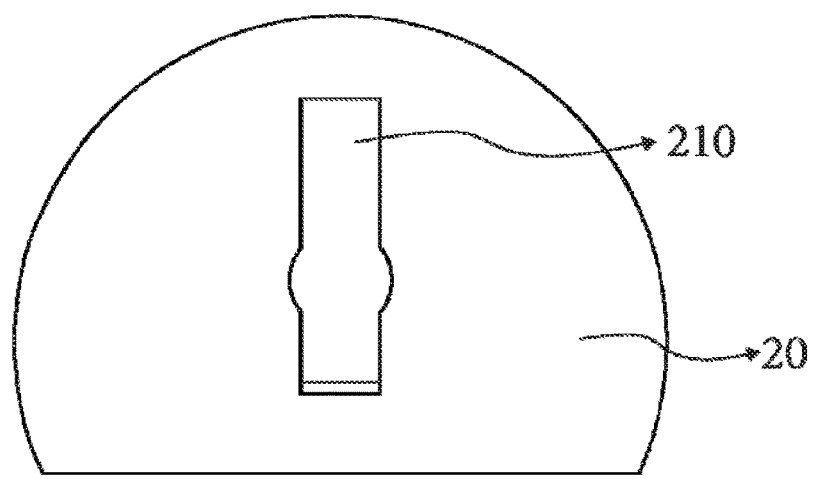
FIG. 6 is a bottom view illustrating a covering part according to Example One of the present disclosure.
Figure 7:
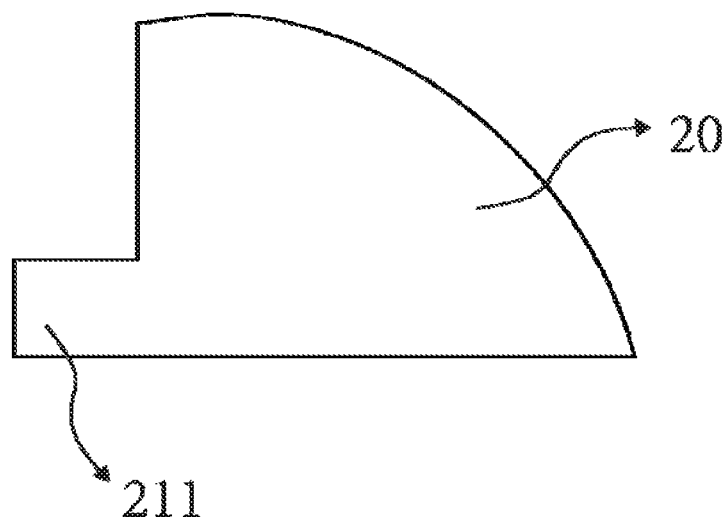
FIG. 7 is a side view illustrating a covering part according to Example One of the present disclosure.
Figure 8:
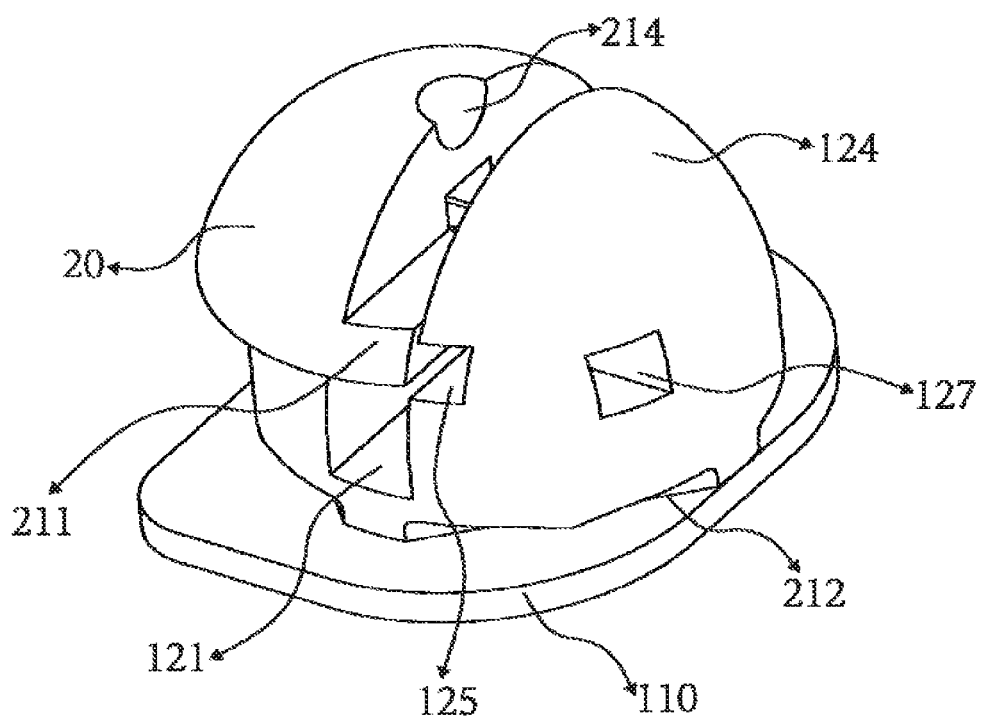
FIG. 8 is a plan view illustrating a main body part and a covering part before assembly according to Example One of the present disclosure.
Figure 9:
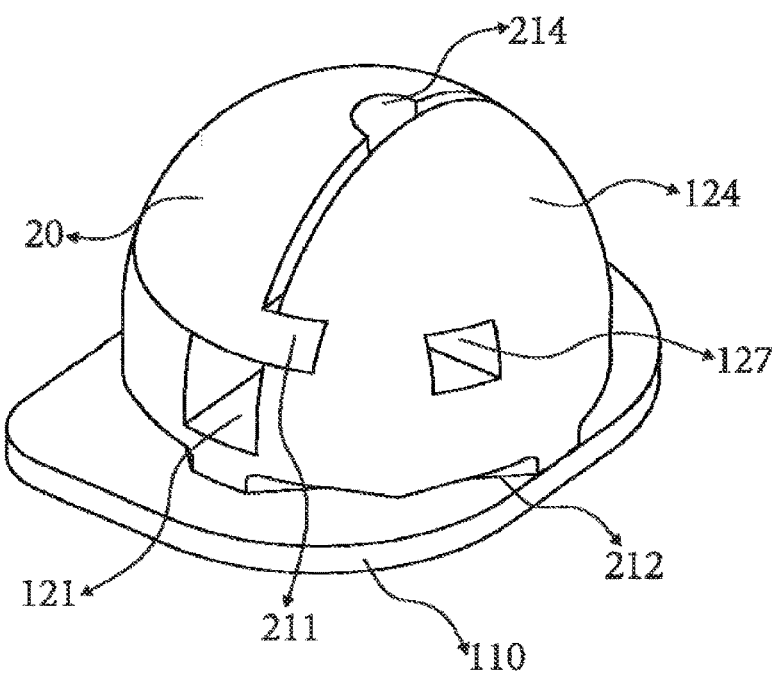
FIG. 9 is a plan view illustrating a main body part and a covering part after being assembled according to Example One of the present disclosure.
Figure 10:
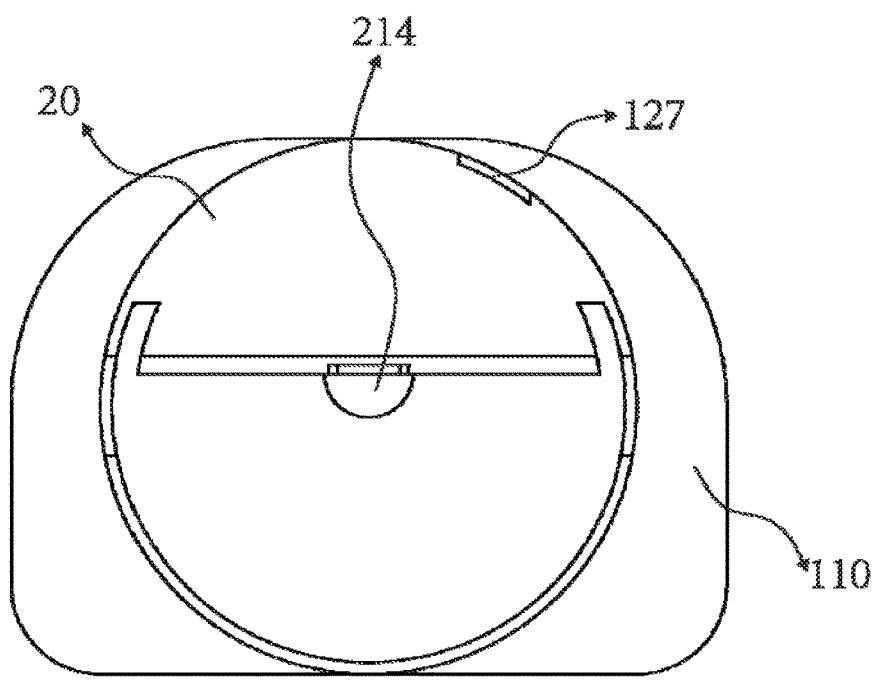
FIG. 10 is a top view illustrating a main body part and a covering part after being assembled according to Example One of the present disclosure.
Figure 11:
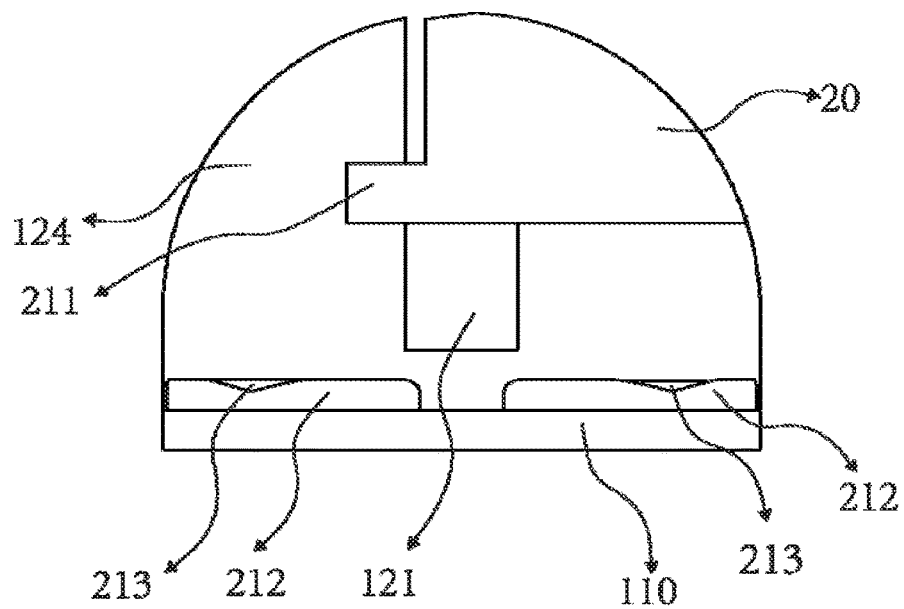
FIG. 11 is a side view illustrating a main body part and a covering part after being assembled according to Example One of the present disclosure.
Figure 12:
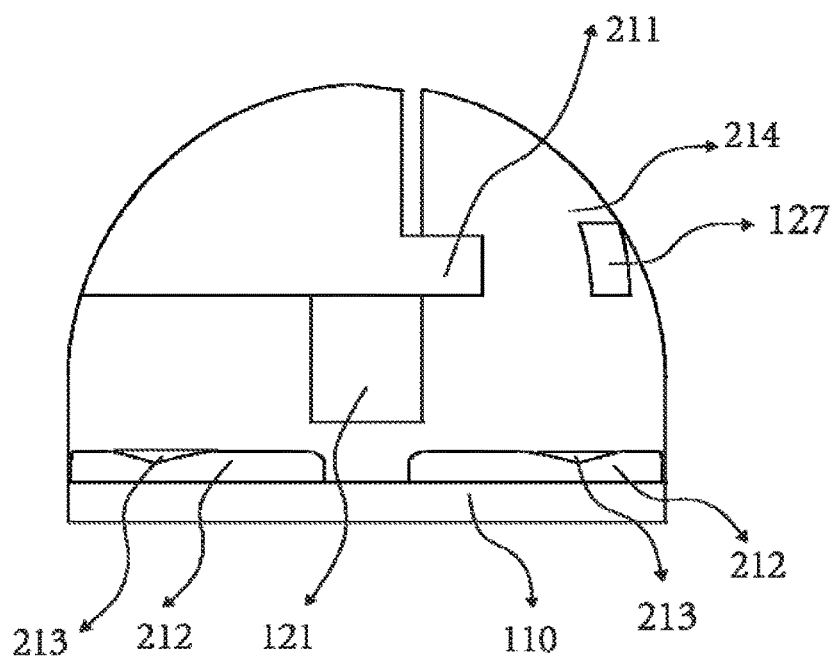
FIG. 12 is a side view illustrating a main body part and a covering part after being assembled according to Example One of the present disclosure.

As shown in FIGS. 1-3, a base plate 110 is connected to the main body part 10. The main body part 10 is fixed on the surface of the base plate 110, the edges of the base plate 110 are of a smooth shape, the bottom face of the base plate 110 is a rough mesh structure, and the bottom face of the base plate 110 is provided with a bonding layer (not shown) which is a specified adhesive. When there is no base plate 110 connected to the bottom of the main body part 10, the bonding layer can be disposed on the bottom of the main body part 10.

The surface of the main body part 10 is provided with a first groove 121 on the radical position of the horizontal section. The first groove 121 can be formed as an arch wire slot, also known as a main slot. The first groove 121 divides the main body part 10 into a first end 122 and a second end 123. The size of the first groove 121 matches with the size of the arch wire. All of edges of the first end 122 of the main body part 10 are protruded such that the surface of the first end 122 of the main body part 10 has a first protruding portion 124. The first protruding portion 124 has a smooth curved surface (on the top of the first protruding portion 124).

The surface of the second end 123 of the main body part 10 is provided with a first bulge 126 to form a stop pin, the first bulge 126 is in a shape of a cylinder, the top end of the first bulge 126 is provided with a ball structure with a diameter larger than that of the first bulge 126. The side surface of the first end 122 of the main body part 10 is provide with a through hole 127 through the first end 122 to form a disassembly hole. The through hole 127 is in a shape of a rectangle, one end of the through hole 127 opens at the second groove 125, and the other end of the through hole 127 opens at the surface of the covering part 20.

As show in FIGS. 4-7, the covering part 20 includes a surface portion and a bottom face portion. The bottom face portion of the covering part 20 matches with the surface of the second end 123 of the main body part 10. The surface portion of the covering part 20 (the top of the covering part 20) is a smooth curved shape. After the covering part 20 engaging with the first protruding portion 124, the surface portion of the covering part 20 matches the surface of the first protruding portion 124 to form a spherical surface. And when the covering part 20 engages with the main body part 10, their side surfaces which face and match each other are in a planar shape, and the outer surface of the covering part 20 and the outer surface of the main body part 10 are both of a smooth curved shape. After the covering part 20 is engaged with the main body part 10 in a matching manner, the bracket has a smooth curved shape in a gingival direction, an occlusal direction, a mesial direction and a distal direction. Specifically, from a labial view, in a gingival direction, an occlusal direction, a mesial direction and a distal direction, when the covering part 20 is engaged with the main body part 10, the surface of the formed bracket has a smooth curved shape. Alternatively, when the covering part 20 is engaged with the main body part 10, the formed bracket has an elliptical shape in the gingival direction, the occlusal direction, the mesial direction and the distal direction, that is, the bracket has an elliptical shape in the 360 degree directions around the outer surface of the main body part and the covering part. Alternatively, the surface of the first protruding portion 124 has a spherical shape, the surface portion of the covering part 20 has a spherical shape, and when the covering part 20 is engaged with the main body part 10, the formed bracket has a spherical shape in the gingival direction, the occlusal direction, the mesial direction and the distal direction, but not limited by geometrical dimensions. Alternatively, the surface of the first protruding portion 124 has a shape of one-fourth of a spherical surface, the surface portion of the covering part 20 has a shape of one-fourth of a spherical surface, and when the covering part 20 is engaged with the main body part 10, the formed bracket has a semi-spherical shape in the gingival direction, the occlusal direction, the mesial direction and the distal direction, but not limited by geometrical dimensions.

In the embodiment, after the surface portion of the covering part 20 matches and is engaged with the surface of the first protruding portion 124, a hemispherical structure may be formed. In other embodiments, the surface portion of the covering part 20 and the surface of the first protruding portion 124 can be curved surfaces of other radians to form an elliptical structure. The side surface of the first protruding portion 124 facing the first groove 121 is provided with a second groove 125 to form a stop groove. The side surface of the covering part 20 facing the main body part 10 is provided with a protruding rim 211 that matches with the second groove 125 to form a fixation protrusion 211.

The bottom face portion of the covering part 20 is provided with a third groove 210 of an elongated shape to form a guide groove. Along the longitudinal direction of the guide groove, a side end of the guide groove opens at a side surface of the covering part 20 facing the main body part 10, and along the transverse direction of the guide groove, the edges of the opening of the guide groove are respectively provided with a flange towards the center of the guide groove to make the size of the opening of the guide groove less than that of the inside of the guide groove. The two opposite elongated flanges are respectively provided with a semicircular concave edge at the side surface of the covering part 20 facing the main body part 10, to form a window that matches with the ball structure of the first bulge 126.

The edge of one side of the main body part 10 facing the surface the base plate 110 is provided with a first recess, and the first recess and the base plate 110 form a fourth groove 212, also known as a ligating groove. There are four fourth grooves 212, and each of the four fourth grooves 212 is evenly distributed on the edge of one side of the main body part 10 facing the surface of the base plate 110. The outer edges of the fourth grooves are respectively provided with a second bulge 213 facing the base plate 110 to form a protection limb to prevent the ligature wire from slipping.

The surface portion of the covering part 20 facing the top of the edge of the main body part 10 is provided with a second recess having a shape of one-fourth of a sphere to form a cover-opening end which is adapted to receive a finger to control the assembly and disassembly of the covering part and the main body part.

In the embodiment, an orthodontics system with a bracket is also provided. The orthodontics system with the bracket includes the bracket as mentioned above, an arch wire, a binder and accessories. There may be a plurality of brackets, and the number of the brackets depends on actual need.

In the embodiment, an orthodontic method based on the above orthodontics system includes:

adjusting the position of the base plate 110 according to the position of the tooth, and adhering and fixing the main body part 10 of the bracket of the orthodontics system onto a surface of the tooth of the patient;

threading the arch wire in the orthodontics system through the first groove 121 of the main body part 10 of each bracket of the orthodontics system in turn;

matching the covering part 20 of the bracket of the orthodontics system with the second end 123 of the main body part 10 of the bracket of the orthodontics system, inserting the first bulge 126 into the window of the third groove 210 corresponding to the ball structure, sliding the covering part 20 towards the first end 122 of the main body part 10, and inserting the fixation protrusion 211 into the second groove 125 of the main body part 10, so that the first groove 121 of the main body part 10 and the arch wire are covered by the covering part 20 and the surface of the first protruding portion of the first end of the main body part corresponds to the surface of the covering part 20; and providing a ligature wire in the fourth groove 212 (ligating groove) of the main body part of each bracket, and fixing the ligature wire on the arch wire.

For the bracket according to the present disclosure, the main body part 10 and the covering part 20 are adapted to match and be engaged with each other, and the smooth curved surface of the first protruding portion 124 and the smooth curved surface portion of the covering part 20 are adapted to match with each other, so that a surface of the bracket facing the mouth and the lips is smooth and without bumps, and does not sting the mucous membrane of the patient's mouth like a bracket with a limb, which will make the patient feel comfortable. Because the bracket according to the present disclosure does not have a protruding limb, food, such as vegetable leaves, may be not retained in the bracket when the patient is eating, which is beneficial for oral health. The smooth curved surface can reduce the accumulation of tartar and dental plaque, and is beneficial for oral cleaning when brushing the teeth, because it is easy to clean the bottom of the bracket. In addition, the bracket according to the present disclosure can decreases the occurrence of demineralization of the tooth around the bracket and caries.

Example Two

In the embodiment, an orthodontics system is provided, including an arch wire and a bracket.

Figure 13:
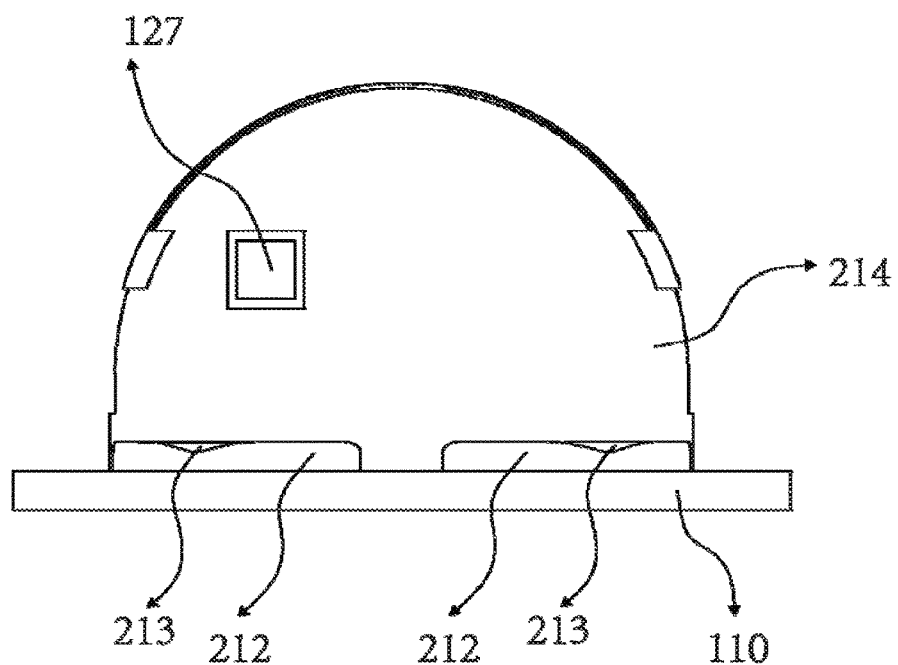
FIG. 13 is a side view illustrating a main body part and a covering part after being assembled in the direction of the through hole of the covering part according to Example One of the present disclosure.
Figure 14:
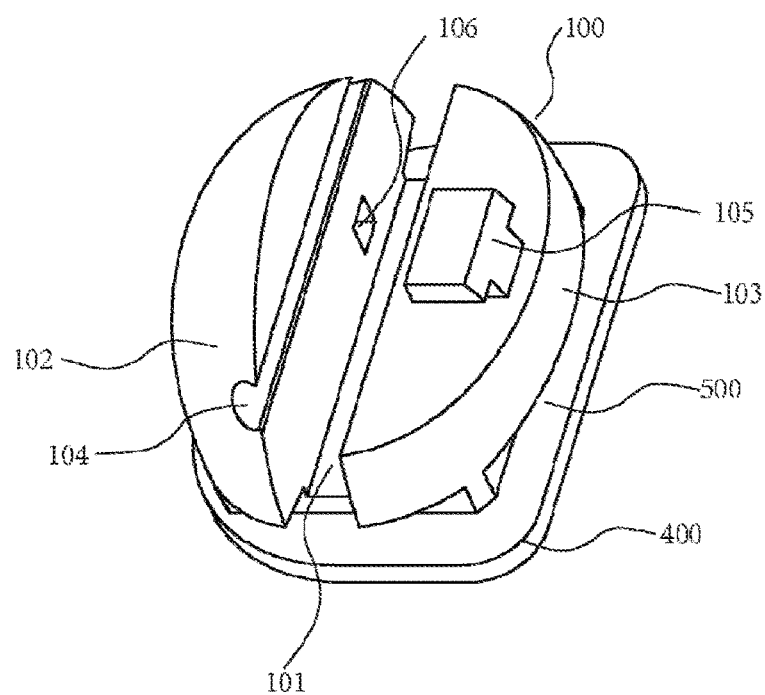
FIG. 14 is a plan view illustrating a main body part and a base plate of a bracket according to Example Two of the present disclosure.
Figure 15:
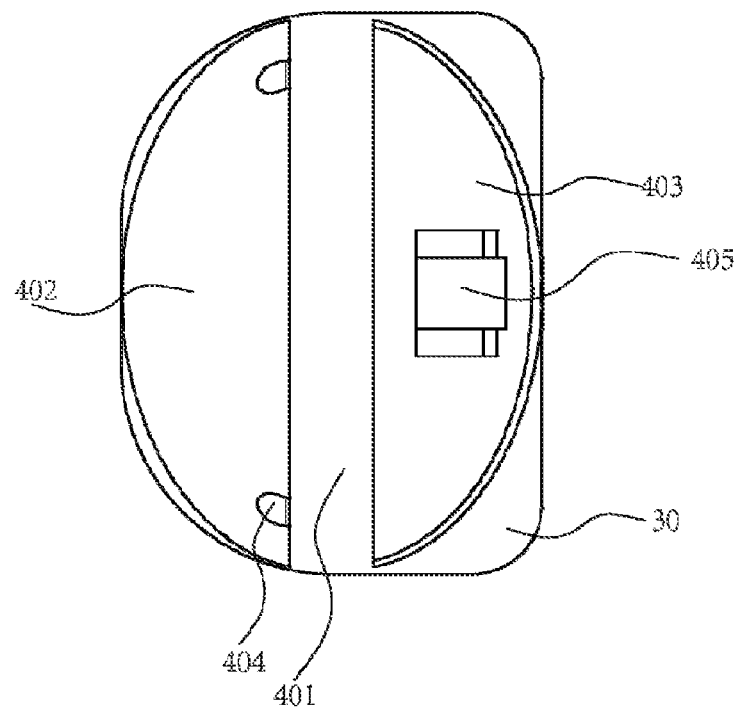
FIG. 15 is a top view illustrating a main body part and a base plate of a bracket according to Example Two of the present disclosure.
Figure 16:
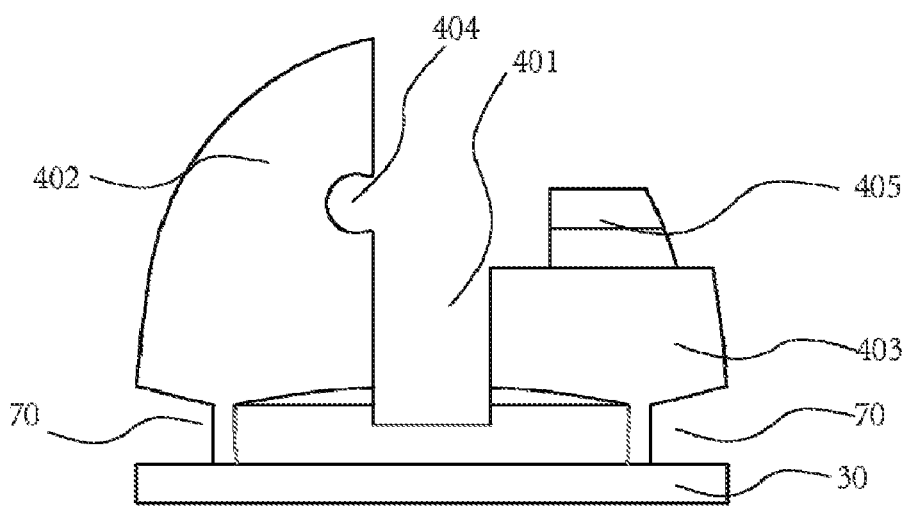
FIGS. 16-19 are respectively a side view illustrating a main body part and a base plate of a bracket according to Example Two of the present disclosure.
Figure 17:
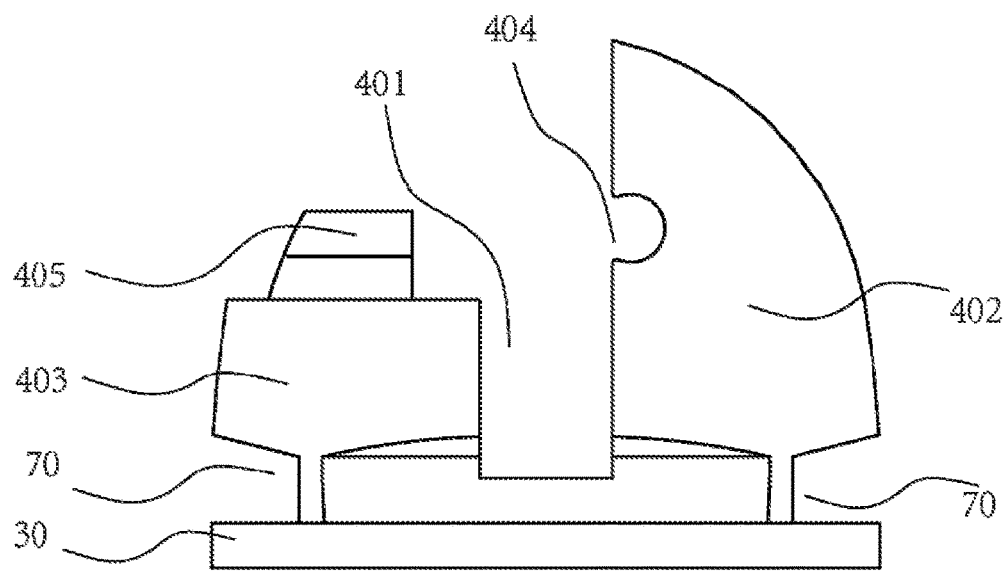
Figure 18:
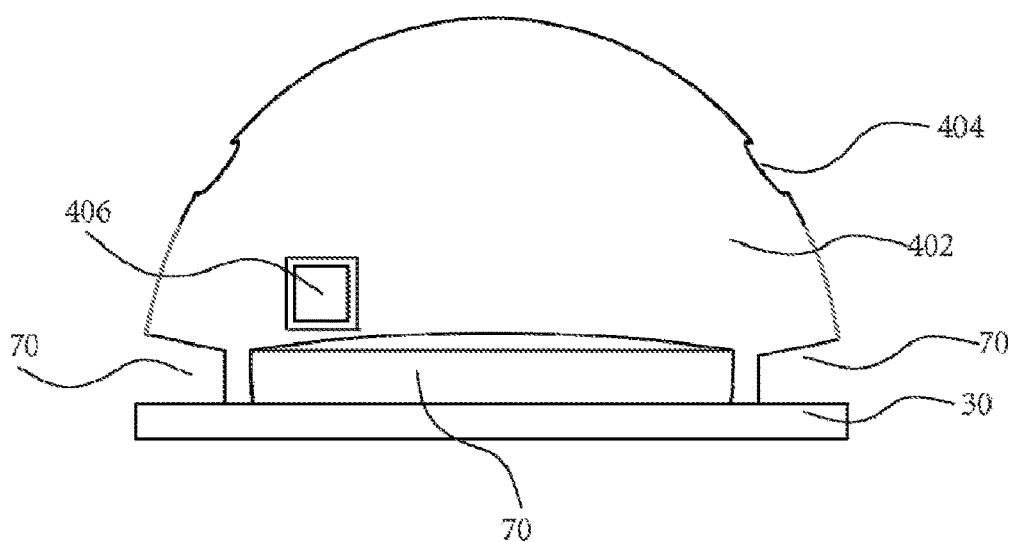
Figure 19:
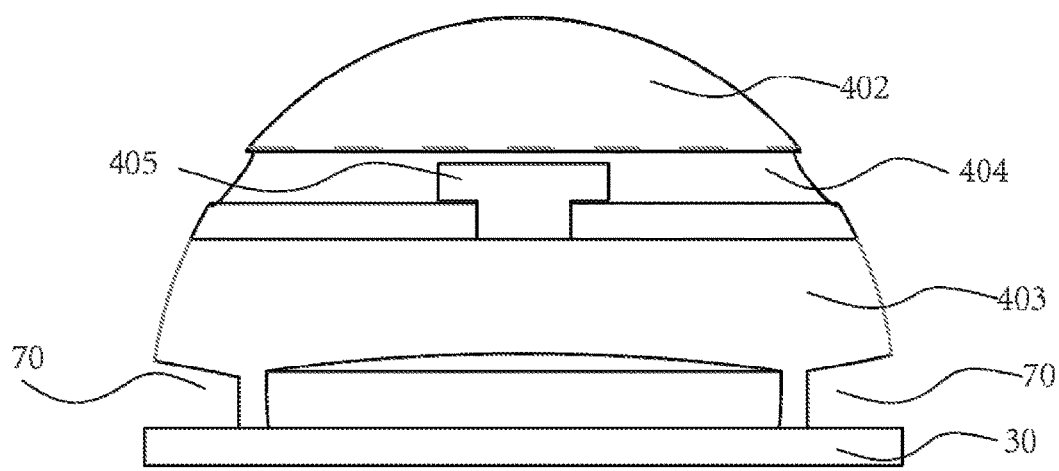
Figure 20:
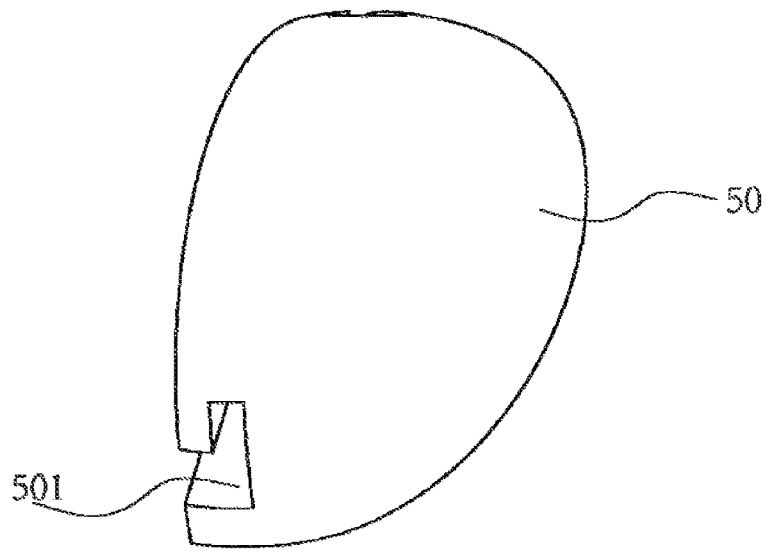
FIG. 20 is a plan view illustrating a covering part of a bracket according to Example Two of the present disclosure.
Figure 21:
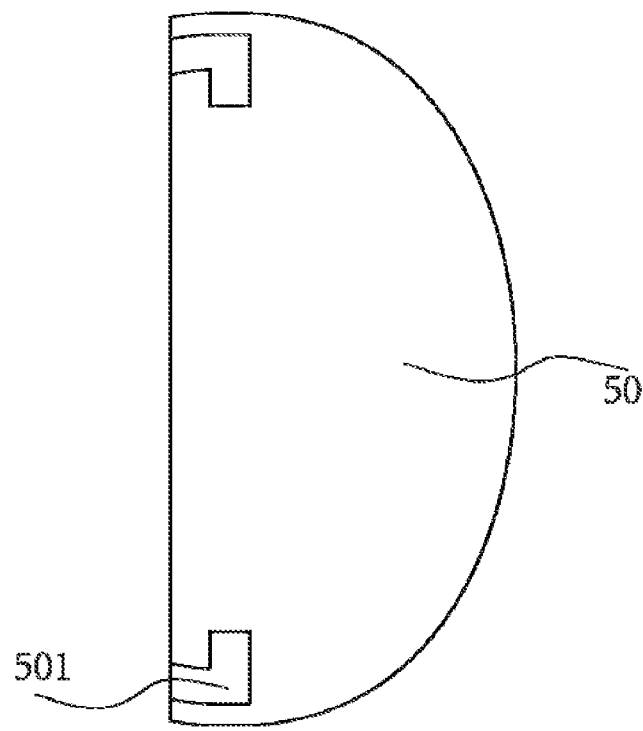
FIG. 21 is a top view illustrating a covering part of a bracket according to Example Two of the present disclosure.
Figure 22:
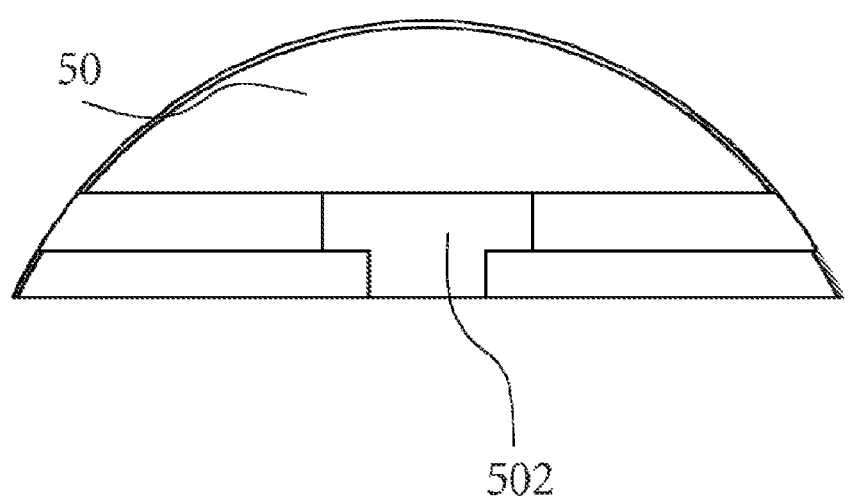
FIGS. 22-23 are respectively a side view illustrating a covering part of a bracket according to Example Two of the present disclosure.
Figure 23:
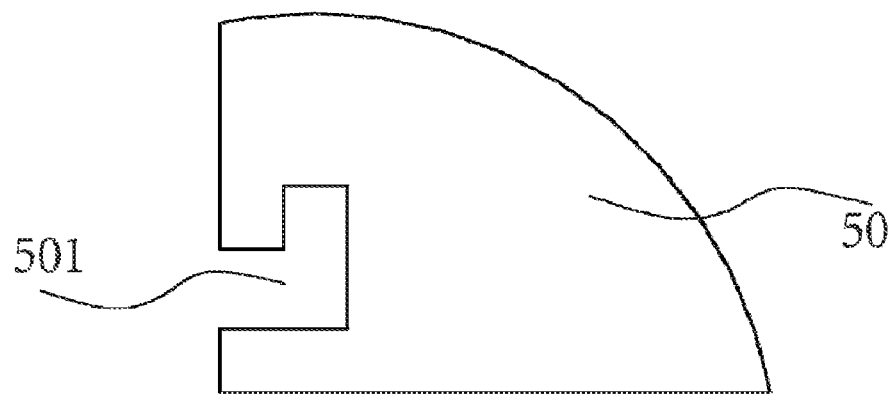

As shown in FIGS. 13-15, the bracket includes a main body part 40, a covering part 50 and a connection part 60.

As shown in FIGS. 14-19, the main body part 40 includes a surface portion and a bottom face portion, the surface portion of the main body part 40 is provided with a first groove 401, also known as a main slot. The first groove 401 divides the main body part 40 into a first end 402 and a second end 403. The size of the main body part 40 in the direction along the first groove 401 is larger than that of the main body part 40 in the direction perpendicular to the first groove 401 in the horizontal plane. Alternatively, the size of the main body part 40 in the direction along the first groove 401 may be less than that of the main body part 40 in the direction perpendicular to the first groove 401 in the horizontal plane. The size of the main body part 40 in the direction along the first groove 401 may be designed according to the width of the tooth. The first end 402 of the main body part 40 is higher than the second end 403, and the first end 402 of the main body part 40 has a smooth curved surface.

As shown in FIGS. 20-23, the covering part includes a surface portion and a bottom face portion, the bottom face portion of the covering part 50 matches with the surface of the second end 403 of the main body part 40, the surface portion of the covering part is smooth and curved, and matches with the surface of the first end portion 402 of the main body part 40 in an approximate ellipsoidal shape. The covering part 50 and the main body part 40 are adapted to match and be engaged with each other to form the bracket that has an approximate ellipsoidal shape in a gingival direction, an occlusal direction, a mesial direction and a distal direction.

The main body part 40 and the covering part 50 are connected by the connection part 60. The arch wire passes through the first groove 401 provided on the surface portion of the main body part 40 in use.

The side surface of the first end 402 of the main body part 40 facing the second end 403 of the main body part 40 is provided with a fifth groove 404, the fifth groove 404 has an opening end and an inner end with a size larger than that of the opening end, and the fifth groove 404 is semicircular in cross section in a direction along the first groove 401.

The side surface of the covering part 50 facing the fifth groove 404 of the main body part 40 is provided with a sixth groove 501, and the sixth groove 501 has an opening end and an inner end with a size larger than that of the opening end.

Figure 24:
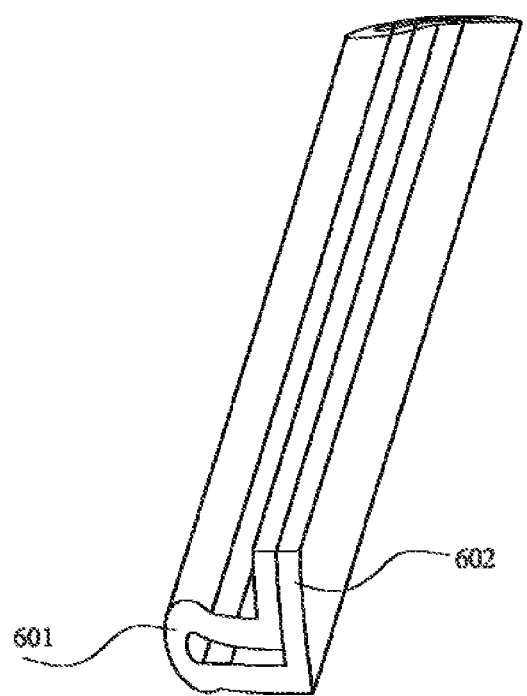
FIG. 24 is a plan view illustrating a connection part of a bracket according to Example Two of the present disclosure.
Figure 25:
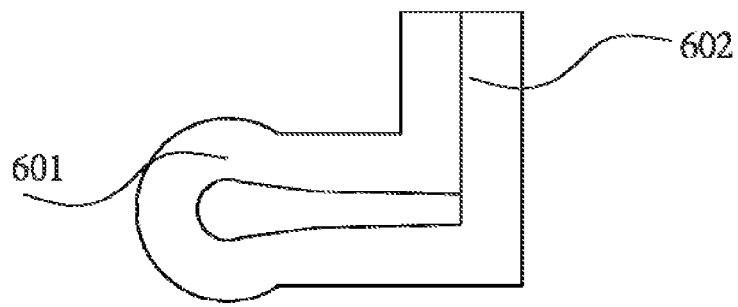
FIG. 25 is a side view illustrating a connection part of a bracket according to Example Two of the present disclosure.
Figure 26:
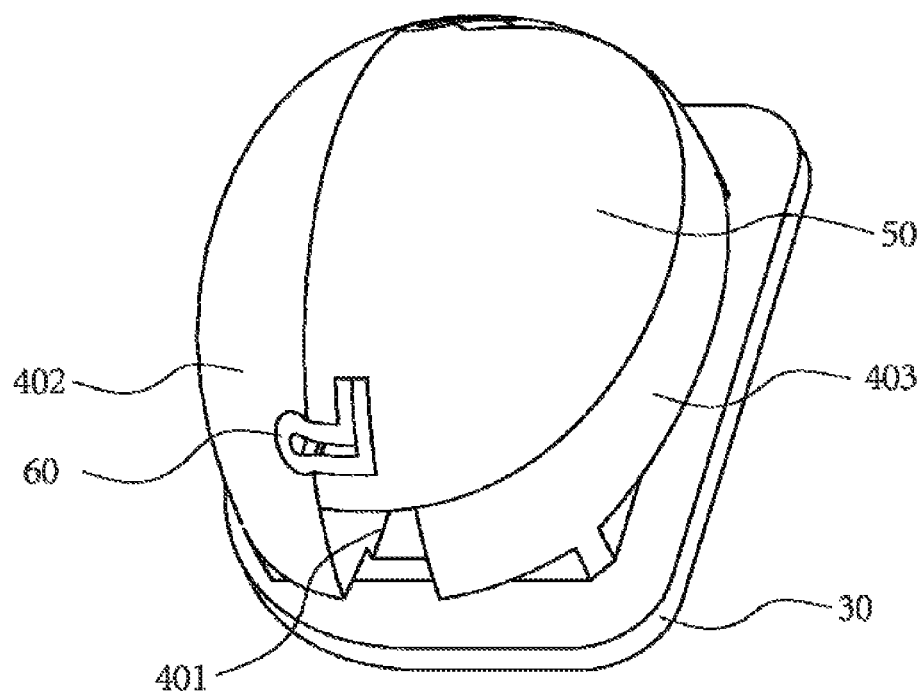
FIG. 26 is a plan view illustrating a bracket according to Example Two of the present disclosure.
Figure 27:
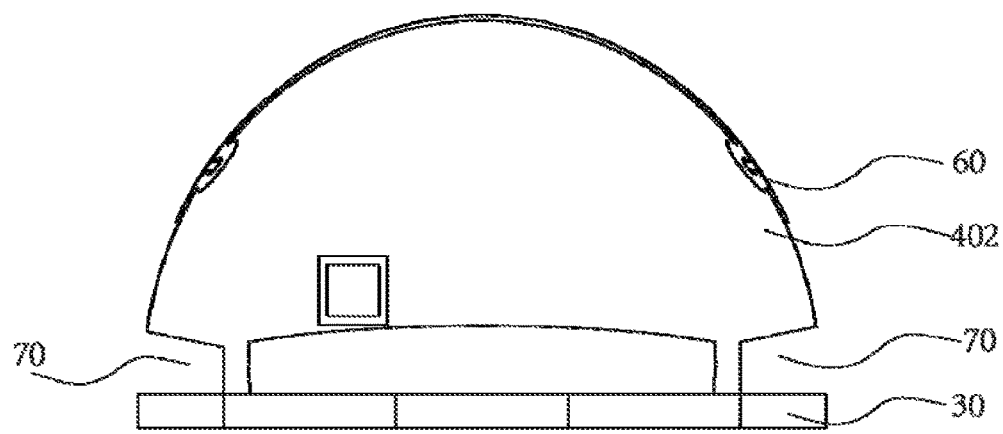
FIGS. 27-28 are respectively a side view illustrating a bracket according to Example Two of the present disclosure.
Figure 28:
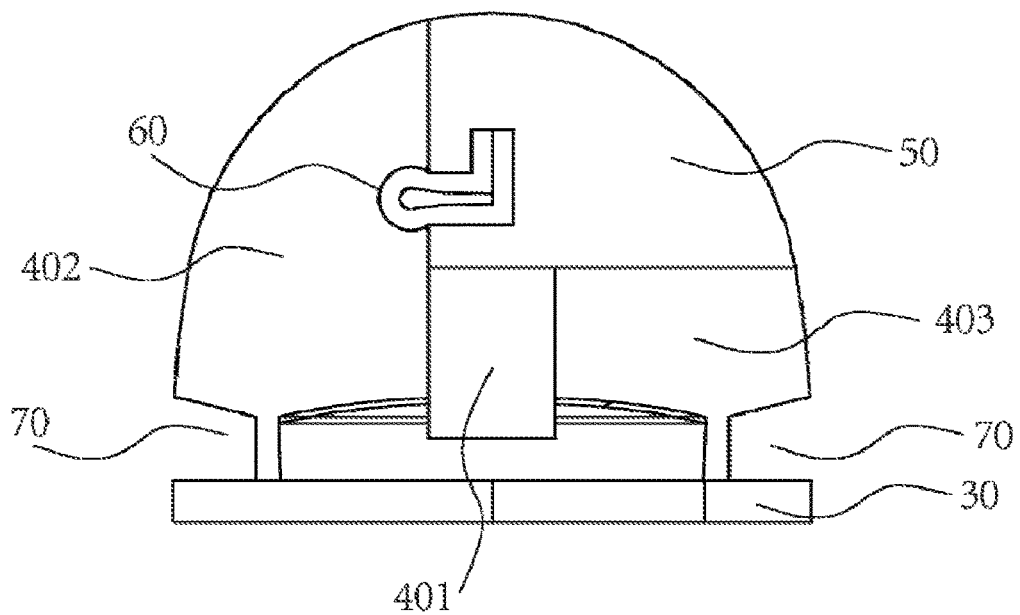

As shown in FIGS. 24-25, the connection part 60 includes a first connection side 601 matching with the fifth groove 404, and a second connection side 602 matching with the sixth groove 501. The sixth groove 501 is rectangular in cross section in a direction along the first groove 401, and one edge of the opening of the sixth groove 501 has a protruding border extending towards the other edge. The first connection side 601 of the connection part 60 has a shape of a semi-cylinder that matches with the semicircular cross section of the fifth groove 404, the second connection side 602 of the connection part has a shape of an L that matches with the sixth groove 501, the first connection side 601 is located at an end of the second connection side 602. In other embodiments, the second connection side 602 may be designed to be in a different shape according to the actual conditions. In the embodiment, the first connection side 601 of the connection part 60 is an elastic structure, and the inside of the first connection side 601 is hollow, so that the first connection side 601 of the connection part 60 can be deformed by pressure and restore to the original shape.

The surface of the second end 403 of the main body part 40 is connected with a second protruding portion 405, and the second protruding portion 405 has a top end and a bottom end with a size less than that of the top end. Both sides of the top of the second protruding portion 405 protrude outwards to make the second protruding portion 405 in a T-shape. The side surface of the covering part 50 facing the first end 402 is provided with a groove portion 502, the groove portion 502 has a first opening on a side surface of the groove portion 502 facing the first end 402, and a second opening on the bottom face portion of the covering part 50, the first opening has a T-shape, and the size of the first opening matches with that of the second protruding portion 405.

The bracket further includes a base plate 30 connected to the bottom of the main body part 40. The bottom of the base plate 30 is provided with a bonding layer. The edge of one side of the bottom face portion of the main body part 40 facing the base plate 30 is provided with a recess, and the recess and the base plate 30 form a ligating groove 70. There may be at least two ligaturing grooves 70, each of the ligaturing grooves 70 is evenly distributed on the edge of one side of the main body part 40 facing the base plate 30, and outer edges of the recess are respectively provided with a bulge facing the base plate 30 to form a protection limb.

Further, the first end 402 of the main body part 40 is provided with a safety hole 406, one end of the safety hole 406 opens at the surface of the first end 402 of the main body part 40, and the other end of the safety hole 406 opens at a side surface of the first end 402 of the main body part 40 facing the covering part 50.

In the embodiment, an orthodontic method based on the above orthodontics system includes:

selecting a set of brackets with different sizes (the size of the main body part 40 in the direction along the first groove 401) according to the arrangement and structure of the teeth of the patient and the widths of the teeth, and adhering and fixing the main body part 40 of the bracket of the orthodontics system onto the surface of the tooth to be corrected by the bonding layer provided on the bottom of the base plate 30; threading the arch wire in the orthodontics system through the first groove 401 of the main body part 40 of the bracket of the orthodontics system; matching and engaging the covering part 50 with the main body part 40; and correcting the teeth by restoring force caused by the deformed arch wire.

If necessary, the arch wire may be fixed in the ligaturing groove 70 by the ligature wire so as to be more firm.

The bracket according to the present disclosure forms an approximate ellipsoidal shape in the direction along the main groove by the matching of the main body part, the covering part and the connection part, especially by providing the size of the main body part in the direction along the main groove larger than that of the main body part in the direction perpendicular to the first groove in the transverse plane (transverse direction). Alternatively, the bracket may be formed in an approximate ellipsoidal shape in the direction along the short-axis of the main groove by providing the size of the main body part in the direction along the main groove less than that of the main body part in the direction perpendicular to the first groove in the transverse plane (transverse direction). The surface portion of the covering part and the surface of the first end of the main body part are in an approximate ellipsoidal shape, so that the length of the main groove can be increased or decreased, the transverse diameter can be increased or decreased, the length of the arch wire controlled by the bracket can be increased, and the control of the axis of the tooth can be improved. In addition, the design of the approximate ellipsoidal shape effectively reduces the surface height of the bracket, improves the comfort of the patient, and reduces the discomfort in the mouth of the patient when in use.

In the bracket according to the present disclosure, a side surface of the first end of the main body part facing the second end of the main body part is provided with a fifth groove, the fifth groove has an opening end and an inner end with a size larger than that of the opening end, a side surface of the covering part facing the fifth groove of the main body part is provided with a sixth groove, and the sixth groove has an opening end and an inner end with a size larger than that of the opening end. The connection part includes a first connection side matching with the fifth groove, and a second connection side matching with the sixth groove. The main body part can be firmly engaged with the covering part by the matching between the fifth groove and the first connection side and the matching between the sixth groove and the second connection side. And it is convenient for assembly and disassembly.

In the bracket according to the present disclosure, the fifth groove is semicircular in cross section in a direction along the first groove. The sixth groove is rectangular in cross section in a direction along the first groove, and one edge of the opening of the sixth groove has a protruding border extending towards the other edge. The first connection side of the connection part has a shape of a semi-cylinder that matches with the semicircular cross section of the fifth groove, the second connection side of the connection part has a shape of an L that matches with the sixth groove. The first connection side corresponding to the fifth groove and the second connection side corresponding to the sixth groove are significantly different in shape, so it is easy to install the connection part in place to avoid incorrect installation.

In the bracket according to the present disclosure, the surface of the second end of the main body part is connected with a second protruding portion of a T-shape. A side surface of the covering part facing the first end is provided with a groove portion of a T-shape. The groove portion matches with the second protruding portion. The design of the second protruding portion and the groove portion make the engagement between the covering part and the main body part more firm, so it is not easy for the covering part to move or fall off during use, and it can reduce the movement of the covering part that may affect the user experience.

In the bracket according to the present disclosure, the design of the ligaturing groove facilitates the ligature wire to be ligatured in the third grooves, and is more helpful in the matching of the bracket and the arch wire. The design of the protection limb can prevent the ligature wire ligatured in the ligaturing groove from dislocating and moving.

In the bracket according to the present disclosure, the first end of the main body part is provided with a safety hole, one end of the safety hole opens at the surface of the first end of the main body part, and the other end of the safety hole opens at a side surface of the first end of the main body part facing the covering part. The design of the safety hole can ensure the bracket is easy to be disassembled. When the covering part cannot be removed from the main body part for some reason, a steel pin may be inserted into the safety hole and pass through the safety hole to reach the covering part, and the covering part may be removed from the main body part by pushing the covering part away from the main body part with the steel pin.

The method for using the bracket according to the present disclosure is convenient in operation, and the device is easy to be produced and operated, low cost and safe in use, and can save time and manpower.

The above are preferred embodiments of the invention described in detail, and should not be deemed as limitations to the scope of the present invention. It should be noted that variations and improvements will become apparent to those skilled in the art to which the present invention pertains without departing from its spirit and scope. Therefore, the scope of the present disclosure is defined by the appended claims.

What is claimed is that:
1. A bracket, comprising:
   a main body part having a first surface portion and a first bottom face portion, wherein the first surface portion includes a first groove dividing the main body part into first and second ends;
   a first protruding portion provided on the first end, wherein the first protruding portion includes a smooth curved first end outside surface;
   a first bulge provided on the second end, wherein the first bulge includes a columnar structure, and a ball structure arranged on the top of the columnar structure; and
   a covering part adapted to engage the main body part to cooperatively form a bracket, the covering part includes:
      a second surface portion having a smooth curved second outside surface; and
      a second bottom face portion that corresponds with a shape of a surface of the second end; and
   an exterior labial surface, cooperatively formed by the main body part and the covering part, wherein the exterior labial surface has a substantially elliptical surface or a substantially spherical surface as a whole in each of a gingival direction, an occlusal direction, a mesial direction and a distal direction.

2. The bracket of claim 1, wherein when the covering part engages the main body part, an inner surface of the covering part and an opposing inner surface of the main body part correspond with each other, and an outer surface of the covering part and an outer surface of the main body part form the exterior labial surface.

3. The bracket of claim 1, wherein a side surface of the first protruding portion facing the first groove is provided with a second groove, and a side surface of the covering part facing the main body part is provided with a protruding rim that corresponds with the second groove.

4. The bracket of claim 3, wherein the first end of the main body part is provided with a through hole, and one end of the through hole opens at the second groove.

5. The bracket of claim 1, wherein the first bulge has a top size larger than its bottom size; and
   the second bottom face portion of the covering part is provided with an elongated groove, wherein the elongated groove has:
      an interior; and
      an opening end with a window for receiving the first bulge,
   wherein the opening end has a smaller width than a width of the interior.

6. The bracket of claim 1, further comprising a base plate having a third surface portion and a third bottom face portion, wherein the main body part is adapted to be fixed on the third surface portion of the base plate; an edge of a side of the main body part facing the third surface portion of the base plate including four first recesses forming four second grooves with the base plate,
   wherein the four second grooves are evenly distributed on the edge of the side of the main body part facing the third surface portion of the base plate.

7. The bracket of claim 6, wherein each first recess has a lower surface with a second bulge extending towards the base plate.

8. The bracket of claim 1, wherein the second surface portion of the covering part facing an edge of the main body part is provided with a recess.

9. An orthodontic system, comprising an arch wire and the bracket of claim 1.

10. A bracket, comprising:
    a main body part having a first surface portion and a first bottom face portion, wherein the first surface portion is provided with a first groove dividing the main body part into first and second ends;

a first protruding portion provided on the first end, wherein the first protruding portion has a smooth curved outside surface;
a covering part adapted to engage the main body part to form a bracket, the covering part includes:
   a second surface portion that is a smooth curved surface; and
   a second bottom face portion that corresponds with a surface of the second end;
an exterior labial surface formed by the main body part and the covering part, wherein the exterior labial surface has a shape selected from the group consisting of a substantially elliptical surface and a substantially spherical surface in each of a gingival direction, an occlusal direction, a mesial direction and a distal direction;
a connection part adapted to connect the main body part and the covering part;
a second groove provided on a side surface of the first end of the main body part facing the second end; and
a third grooved provided on a side surface of the covering part facing the second groove;
   wherein the connection part includes:
      a first connection side matching with the second groove; and
      a second connection side matching with the third groove.

11. The bracket of claim 10, wherein the second groove has a cross-sectional shape of a major arc with an opening width smaller than a diameter of the major arc.

12. The bracket of claim 10, wherein the third groove has a rectangular cross-sectional shape, and one edge of an opening of the third groove has a protruding border extending towards another edge; and
   the first connection side of the connection part has a shape of a semi-cylinder that matches with the cross-sectional shape of the second groove, the second connection side of the connection part has an L-shape that matches with the third groove, the first connection side being located at an end of the second connection side.

13. The bracket of claim 10, wherein a second protruding portion is connected to the surface of the second end of the main body part, the second protruding portion including an upper portion and a lower portion having a smaller sectional area than the upper portion; and
   a side surface of the covering part towards the first end is provided with a groove portion, the groove portion has a first opening on a side surface of the groove portion facing the first end, and a second opening on the second bottom face portion of the covering part, and the size of the first opening matches with that of the second protruding portion.

14. The bracket of claim 13, wherein both sides of the upper portion of the second protruding portion protrude outwards such that the second protruding portion is T-shaped, and the first opening is T-shaped.

15. The bracket of claim 10, further comprising a base plate connected to the first bottom face portion of the main body part, an edge of a bottom side of the main body part facing the base plate is provided with recesses forming ligating grooves with the base plate; and
   there are four ligating grooves evenly distributed on the edge of the bottom side of the main body part facing the base plate, and each recess has a top with a bulge extending towards the base plate to form a protection limb.

16. The bracket of claim 10, wherein the first end of the main body part is provided with a safety hole, one end of the safety hole opens at a surface of the first end of the main body part, and the other end of the safety hole opens at a side surface of the first end of the main body part facing the covering part.

* * * * *